United States Patent
Freeman et al.

(10) Patent No.: US 7,001,344 B2
(45) Date of Patent: Feb. 21, 2006

(54) BLOOD SAMPLING DEVICE WITH DIAPHRAGM ACTUATED LANCET

(75) Inventors: Dominique M. Freeman, La Honda, CA (US); Vladimir Drbal, Belmont, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 266 days.

(21) Appl. No.: 10/173,236

(22) Filed: Jun. 12, 2002

(65) Prior Publication Data

US 2003/0088191 A1     May 8, 2003

Related U.S. Application Data

(60) Provisional application No. 60/298,061, filed on Jun. 12, 2001.

(51) Int. Cl.
*A61B 5/00* (2006.01)

(52) U.S. Cl. .................................................. 600/583

(58) Field of Classification Search ................ 600/573, 600/309, 574–584; 606/180–182, 171; 206/569; 604/115, 22
See application file for complete search history.

(56) References Cited

U.S. PATENT DOCUMENTS

| | | | |
|---|---|---|---|
| 2,714,890 A | 8/1955 | Vang ............................ | 128/305 |
| 3,086,288 A | 4/1963 | Balamuth et al. .............. | 30/272 |
| 3,208,452 A | 9/1965 | Stern ........................... | 128/315 |
| 3,673,475 A | 6/1972 | Britton, Jr. ................... | 318/122 |
| 3,832,776 A | 9/1974 | Sawyer ......................... | 30/272 |
| 4,077,406 A | 3/1978 | Sandhage et al. ........... | 128/217 |
| 4,154,228 A | 5/1979 | Feldstein et al. ........... | 128/329 |
| 4,203,446 A | 5/1980 | Höfert et al. ................ | 128/329 |
| 4,223,674 A | 9/1980 | Fluent et al. ................ | 128/217 |
| 4,230,118 A | 10/1980 | Holman et al. | |
| 4,356,826 A | 11/1982 | Kubota ......................... | 128/630 |
| 4,449,529 A | 5/1984 | Burns et al. ................. | 128/314 |
| 4,462,405 A | 7/1984 | Ehrlich ......................... | 128/329 |
| 4,518,384 A | 5/1985 | Tarello et al. ................ | 604/61 |
| 4,535,773 A | 8/1985 | Yoon ............................ | 604/51 |
| 4,553,541 A | 11/1985 | Burns | |
| 4,627,445 A | 12/1986 | Garcia et al. ................ | 128/770 |
| 4,637,403 A | 1/1987 | Garcia et al. ................ | 128/770 |
| 4,653,513 A * | 3/1987 | Dombrowski ............... | 600/578 |
| 4,750,489 A | 6/1988 | Berkman et al. ........... | 128/314 |
| 4,787,398 A | 11/1988 | Garcia et al. ................ | 128/770 |
| 4,794,926 A | 1/1989 | Munsch et al. ............. | 128/314 |
| 4,823,806 A | 4/1989 | Bajada ......................... | 128/744 |
| 4,924,879 A | 5/1990 | O'Brien ....................... | 128/770 |
| 4,983,178 A | 1/1991 | Schnell | |
| 4,995,402 A | 2/1991 | Smith et al. ................. | 128/771 |

(Continued)

FOREIGN PATENT DOCUMENTS

| WO | WO 01/00090 A1 | 1/2001 |
|---|---|---|
| WO | WO 01/66010 A1 | 9/2001 |
| WO | WO 02/056769 A1 | 7/2002 |

*Primary Examiner*—Max F. Hindenburg
*Assistant Examiner*—Brian Szmal
(74) *Attorney, Agent, or Firm*—Heller Ehrman LLP

(57) ABSTRACT

A device and method to obtain a blood sample in a sealed configuration. The device includes a sampling assembly having a driver, a lancet, and a blood reservoir, and a pad having a proximal side and a distal side. The proximal side of the pad conforms to the shape of a skin area, and the distal side is attached to the sampling assembly. The pad and the sampling assembly are configured to provide a sealed configuration around the skin area for transferring blood from the skin area to the blood reservoir.

30 Claims, 4 Drawing Sheets

U.S. PATENT DOCUMENTS

| | | | |
|---|---|---|---|
| 5,029,583 A | 7/1991 | Meserol et al. | 128/633 |
| 5,035,704 A | 7/1991 | Lambert et al. | 606/182 |
| 5,047,044 A | 9/1991 | Smith et al. | 606/182 |
| 5,097,810 A | 3/1992 | Fishman et al. | 128/743 |
| 5,145,565 A | 9/1992 | Kater et al. | 204/153.1 |
| 5,152,775 A | 10/1992 | Ruppert | 606/182 |
| 5,188,118 A | 2/1993 | Terwilliger | 128/753 |
| 5,189,751 A | 3/1993 | Giuliani et al. | 15/22.1 |
| 5,222,504 A | 6/1993 | Solomon | 128/744 |
| 5,231,993 A | 8/1993 | Haber et al. | 128/770 |
| 5,279,294 A | 1/1994 | Anderson et al. | 128/633 |
| 5,318,583 A | 6/1994 | Rabenau et al. | |
| 5,320,607 A * | 6/1994 | Ishibashi | 604/115 |
| 5,320,808 A | 6/1994 | Holen et al. | 422/64 |
| 5,368,047 A | 11/1994 | Suzuki et al. | 128/765 |
| 5,395,387 A | 3/1995 | Burns | |
| 5,415,169 A | 5/1995 | Siczek et al. | 128/653.1 |
| 5,472,427 A | 12/1995 | Rammler | 604/164 |
| 5,474,084 A | 12/1995 | Cunniff | 128/744 |
| 5,510,266 A | 4/1996 | Bonner et al. | |
| 5,514,152 A | 5/1996 | Smith | 606/182 |
| 5,529,074 A | 6/1996 | Greenfield | 128/744 |
| 5,575,403 A | 11/1996 | Charlton et al. | 221/31 |
| 5,630,986 A | 5/1997 | Charlton et al. | 422/64 |
| 5,632,410 A | 5/1997 | Moulton et al. | 221/79 |
| 5,662,127 A * | 9/1997 | De Vaughn | 600/578 |
| 5,700,695 A | 12/1997 | Yassinzadeh et al. | 436/180 |
| 5,714,390 A | 2/1998 | Hallowitz et al. | 436/526 |
| 5,720,924 A | 2/1998 | Eikmeier et al. | 422/102 |
| 5,738,244 A | 4/1998 | Charlton et al. | 221/26 |
| 5,758,643 A | 6/1998 | Wong et al. | 128/632 |
| 5,776,157 A | 7/1998 | Thorne et al. | 606/182 |
| 5,788,651 A | 8/1998 | Weilandt | 600/567 |
| 5,801,057 A | 9/1998 | Smart et al. | 436/68 |
| 5,810,199 A | 9/1998 | Charlton et al. | 221/31 |
| 5,823,973 A | 10/1998 | Racchini et al. | 600/573 |
| 5,830,219 A | 11/1998 | Bird et al. | 606/130 |
| 5,846,490 A | 12/1998 | Yokota et al. | 422/66 |
| 5,854,074 A | 12/1998 | Charlton et al. | 436/46 |
| 5,855,801 A | 1/1999 | Lin et al. | 216/2 |
| 5,863,800 A | 1/1999 | Eikmeier et al. | 436/48 |
| 5,871,494 A | 2/1999 | Simons et al. | 606/181 |
| 5,879,311 A | 3/1999 | Duchon et al. | 600/583 |
| 5,880,829 A | 3/1999 | Kauhaniemi et al. | 356/246 |
| 5,885,211 A | 3/1999 | Eppstein et al. | 600/309 |
| 5,891,053 A | 4/1999 | Sesekura | 600/583 |
| 5,916,229 A | 6/1999 | Evans | 606/171 |
| 5,938,679 A | 8/1999 | Freeman et al. | 606/181 |
| 5,951,582 A | 9/1999 | Thorne et al. | 606/182 |
| 5,968,063 A | 10/1999 | Chu et al. | 606/185 |
| 5,971,941 A | 10/1999 | Simons et al. | 600/573 |
| 5,997,561 A | 12/1999 | Böcker et al. | 606/182 |
| 6,027,459 A | 2/2000 | Shain et al. | 600/573 |
| 6,036,924 A | 3/2000 | Simons et al. | 422/100 |
| 6,048,352 A | 4/2000 | Douglas et al. | 606/181 |
| 6,071,294 A | 6/2000 | Simons et al. | 606/181 |
| 6,093,156 A | 7/2000 | Cunningham et al. | 600/573 |
| 6,117,630 A | 9/2000 | Reber et al. | 435/4 |
| 6,120,462 A | 9/2000 | Hibner et al. | 600/566 |
| 6,132,449 A | 10/2000 | Lum et al. | 606/181 |
| 6,136,013 A | 10/2000 | Marshall et al. | 606/167 |
| 6,139,562 A | 10/2000 | Mauze et al. | 606/171 |
| 6,143,164 A | 11/2000 | Heller et al. | 205/777.5 |
| 6,152,942 A | 11/2000 | Brenneman et al. | 606/181 |
| 6,155,992 A | 12/2000 | Henning et al. | 600/583 |
| 6,156,051 A | 12/2000 | Schraga | 606/181 |
| 6,159,424 A | 12/2000 | Kauhaniemi et al. | 422/63 |
| 6,171,325 B1 * | 1/2001 | Mauze et al. | 606/171 |
| 6,176,865 B1 | 1/2001 | Mauze et al. | 606/171 |
| 6,183,489 B1 | 2/2001 | Douglas et al. | 606/181 |
| 6,193,673 B1 | 2/2001 | Viola et al. | 600/568 |
| 6,203,504 B1 | 3/2001 | Latterell et al. | 600/576 |
| 6,206,841 B1 | 3/2001 | Cunningham et al. | |
| 6,210,420 B1 | 4/2001 | Mauze et al. | 606/182 |
| 6,210,421 B1 | 4/2001 | Böcker et al. | 606/182 |
| 6,228,100 B1 | 5/2001 | Schraga | 606/183 |
| 6,231,531 B1 | 5/2001 | Lum et al. | 601/46 |
| 6,261,241 B1 | 7/2001 | Burbank et al. | 600/564 |
| 6,261,245 B1 | 7/2001 | Kawai et al. | 600/576 |
| 6,283,926 B1 | 9/2001 | Cunningham et al. | 600/573 |
| 6,285,454 B1 | 9/2001 | Douglas et al. | 356/446 |
| 6,306,104 B1 | 10/2001 | Cunningham et al. | 600/573 |
| 6,306,152 B1 | 10/2001 | Verdonk et al. | 606/182 |
| 6,315,738 B1 | 11/2001 | Nishikawa et al. | 600/583 |
| 6,319,210 B1 | 11/2001 | Douglas et al. | 600/583 |
| 6,332,871 B1 | 12/2001 | Douglas et al. | 600/583 |
| 6,352,514 B1 | 3/2002 | Douglas et al. | 600/583 |
| 6,364,889 B1 | 4/2002 | Kheiri et al. | 606/181 |
| 6,364,890 B1 | 4/2002 | Lum et al. | 606/181 |
| 6,375,627 B1 | 4/2002 | Mauze et al. | 600/584 |
| 6,379,317 B1 | 4/2002 | Kintzig et al. | 600/573 |
| 6,379,969 B1 | 4/2002 | Mauze et al. | 436/68 |
| 6,391,005 B1 | 5/2002 | Lum et al. | 604/117 |
| 6,402,701 B1 | 6/2002 | Kaplan et al. | 600/567 |
| 6,402,704 B1 | 6/2002 | McMorrow | 600/576 |
| 6,409,740 B1 | 6/2002 | Kuhr et al. | 606/182 |
| 6,461,496 B1 | 10/2002 | Feldman et al. | 205/777 |
| 6,472,220 B1 | 10/2002 | Simons et al. | 436/63 |
| 6,485,439 B1 | 11/2002 | Roe et al. | 600/578 |
| 6,488,891 B1 | 12/2002 | Mason et al. | 422/58 |
| 6,491,709 B1 | 12/2002 | Sharma et al. | 606/181 |
| 6,497,845 B1 | 12/2002 | Sacherer | 422/104 |
| 6,503,210 B1 | 1/2003 | Hirao et al. | 600/576 |
| 6,506,575 B1 | 1/2003 | Knappe et al. | 435/25 |
| 6,530,892 B1 | 3/2003 | Kelly | |
| 2001/0031931 A1 | 10/2001 | Cunningham et al. | 600/573 |
| 2002/0002344 A1 | 1/2002 | Douglas et al. | 600/583 |
| 2002/0004196 A1 | 1/2002 | Whitson | 435/4 |
| 2002/0052618 A1 | 5/2002 | Haar et al. | 606/181 |
| 2002/0082543 A1 | 6/2002 | Park et al. | 604/21 |
| 2002/0103499 A1 | 8/2002 | Perez et al. | 606/182 |
| 2002/0169394 A1 * | 11/2002 | Eppstein et al. | 600/573 |
| 2003/0083685 A1 | 5/2003 | Freeman et al. | |
| 2003/0191376 A1 * | 10/2003 | Samuels et al. | 600/309 |

\* cited by examiner

BLOOD SAMPLING DEVICE WITH DIAPHRAGM ACTUATED LANCET

RELATED APPLICATIONS

This application is related to and claims priority from U.S. Provisional Patent Application entitled "Blood Sampling device with Diaphragm Actuated Lancet", to Drbal et al., filed Jun. 12, 2001, Ser. No. 60/298,061.

BACKGROUND

This invention relates to medical devices, and more particularly to a blood sampling device which is capable of drawing the blood sample in a sealed configuration.

Lancing devices are known in the medical health-care products industry for piercing the skin to produce blood for analysis. Biochemical analysis of blood samples may be used as a diagnostic tool for determining clinical information. Many point-of-care tests are performed directly on capillary whole blood, which is typically obtained by making a small incision in the fingertip, creating a wound, which generates a blood droplet on the surface of the skin.

Conventional methods of lancing may include piercing or slicing the skin with a needle or razor. These methods may utilize lancing devices that contain a multitude of spring, cam and mass actuators to drive the lancet. Some devices may not integrate lancing and blood sample collection, but require the user to transfer the blood sample to the analysis device by exposing the lanced finger to air. Other devices lance the skin and collect the blood sample, but require suctioning ambient air along with the blood sample. Therefore, a method using the conventional device may lance the skin, but upon retraction may require the user to transport the blood sample from the finger to some type of blood analysis device or to suction the blood sample from the finger's surface. Accordingly, conventional methods of blood sampling may require several steps. Initially, the paraphernalia is assembled by loading a sterile lancet, loading a test strip, and arming the launcher. The intended target skin area, such as finger, is placed against the lancet launcher. The launcher is then activated using the other hand. Finally, the launcher is set aside and the lanced finger is placed against a test strip.

The problem with these conventional devices is that the blood sample may become exposed to ambient air and thus may contaminate the sample with ambient air including oxygen, nitrogen, other environmental gases. This may substantially compromise accurate gas analysis of the blood sample when conducting in vitro testing of the blood.

SUMMARY

Embodiments of the present invention relate to medical devices and to methods for obtaining blood for chemical analysis. More particularly, embodiments of the invention relate to devices and methods for piercing the skin (lancing) and obtaining a blood sample within a sealed configuration.

In one aspect of the invention, a blood sample is acquired from a patient in a sealed configuration using a blood sampling device. The sampling device includes an assembly having a driver, a lancet, and a blood reservoir, and a pad. The pad has a proximal side and a distal side. The proximal side conforms to the shape of a skin area, and the distal side attaches to the sampling assembly. Thus, the pad and the sampling assembly are configured to provide a sealed configuration around the skin area for transferring blood from the skin area to the reservoir.

In another aspect of the invention, a blood sample is acquired from a patient in a sealed configuration using a method which integrates lancing and sample collection and allowing for blood gas testing from the sample. This may be achieved by positioning a skin area to be lanced on a pad, and applying a force on the skin area to allow the pad to conform to the shape of the skin area, such that the pad forms a sealed configuration around the skin area. The skin area is then lanced through the pad. A blood sample is drawn from the lanced skin area through the pad to collect the blood sample in a sealed configuration without substantially exposing the blood sample to ambient air.

In a further aspect of the invention, a blood sample is automatically acquired from a patient in a sealed configuration using a computer readable medium containing executable instructions which when executed in a processing system, performs lancing operation and obtains a blood sample from a finger tip in a sealed configuration. The executable instructions include sensing to confirm that a sealed configuration around a skin area has been formed to transfer blood from the skin area into a blood reservoir without exposing the blood to ambient air, lancing the skin area within the sealed configuration, and transferring the blood sample from the lanced skin area in the sealed configuration.

DETAILED DESCRIPTION

In recognition of the above-stated problems associated with conventional blood sampling devices, embodiments for using a blood sampling device that pierces the skin (lancing) and obtains a blood sample without substantial exposure to ambient air to enable gas analysis of the sample are described. In particular, the blood sampling device is coupled to the skin area (e.g. finger) through a pad to form a sealed or closed configuration. Hence, the pad applied to the skin area seals the area to be lanced so that the skin area is not substantially exposed to ambient air. The pad also provides a seal for the blood sample being transferred from the lanced skin area to a blood reservoir in the sampling device. Furthermore, the blood sampling device is configured as an integrated device that integrates the lancing and blood sample collection so that the device may capture and transport the capillary blood from the wound created by a lancet to a blood reservoir without exposure to ambient air. A valve system and driver in the sampling device may allow the user to drive the lancet on the compression of the driver (e.g. diaphragm) and suction the blood through the pad on the depression of the driver. Consequently, for purposes of illustration and not for purposes of limitation, the exemplary embodiments of the invention are described in a manner consistent with such use, though clearly the invention is not so limited.

Figure 1:
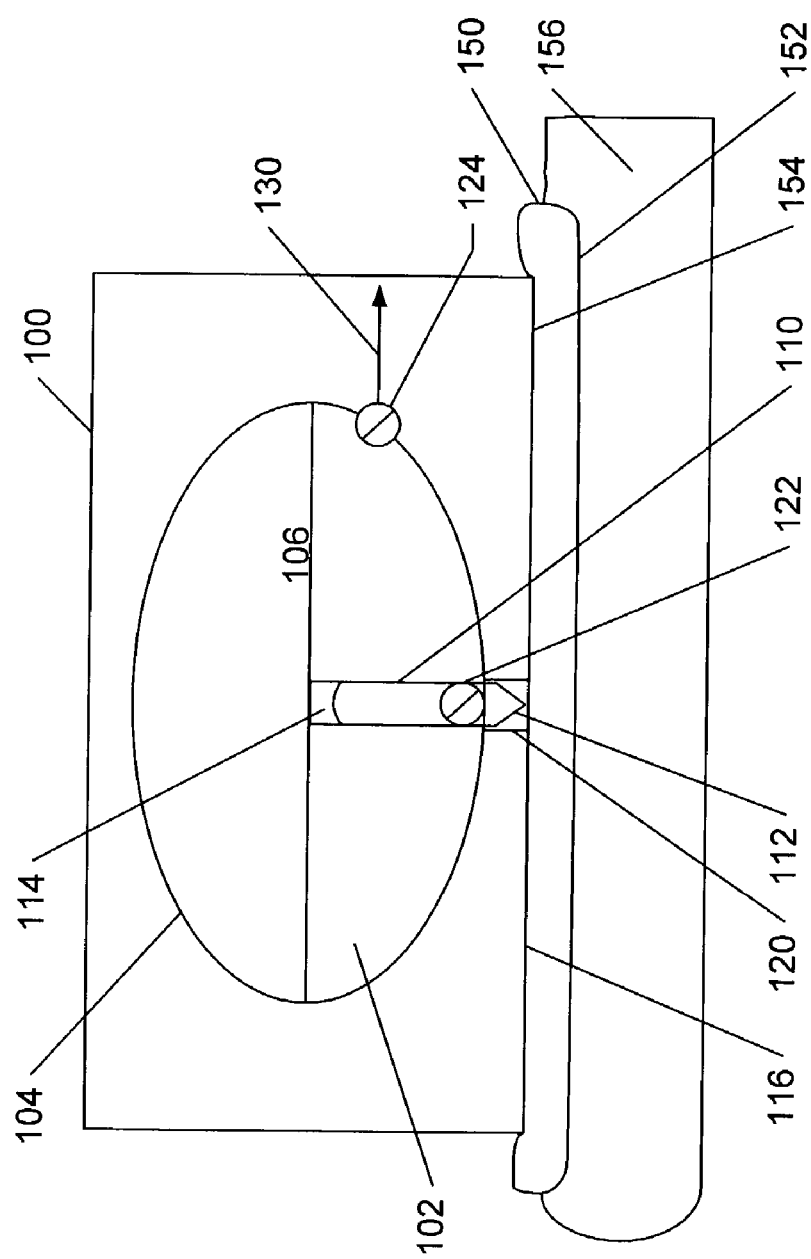
FIG. 1 illustrates a cut-away side view of a sampling assembly attached to a finger pad in accordance with an embodiment of the invention.

A sampling assembly 100 coupled to a finger pad 150 in a sealed configuration in accordance with an embodiment of the invention is shown in FIG. 1. The sampling assembly 100 includes a reservoir 102 formed by a portion of an elliptical chamber 104 and a driver 106. However, in an alternative embodiment, the chamber 104 may be designed to be spherical, cubical, or any other appropriate shape for storing the blood sample. The sampling assembly 100 also includes a lancet 110 disposed within an opening 120, which couples the chamber 104 with lanced skin area through the finger pad 150. The sampling assembly 100 may further include at least one valve 122, 124 for drawing and transferring the blood sample from the lanced skin area for blood analysis. In the illustrated embodiment, the valve 122 is configured as a sample inflow check valve while the valve 124 is configured as a sample outflow check valve. Check valve as used in the above context is a valve that allows flow in one direction only. Hence, the valve 122 connects the reservoir 102 with the blood inflow conduit (i.e. the opening 120) while the valve 124 connects the reservoir 102 with the blood outflow conduit 130.

In FIG. 1, the finger pad 150 is coupled to the sampling assembly 100, in a sealed configuration, along the bottom surface 116. However, in some embodiments, the pad 150 may be coupled to the sampling assembly 100 along any appropriate surface. The finger pad 150 has a proximal side 152 and a distal side 154 with proximal side 152 conforming to the user's finger 156. Therefore, the blood sampling assembly 100 is coupled to the finger 156 through the pad 150 to form a sealed or closed system. Accordingly, the pad 150 applied to the finger 156 seals the area to be lanced so that the finger 156 is not substantially exposed to ambient air. The finger pad 150 also provides a seal for the blood sample being transferred from the lanced area of the finger to the blood reservoir 102.

In one embodiment, the finger pad 150 may include an elastomer. Furthermore, the elastomer 150 may be formed of relatively soft durometer type compounds, such as silicone rubber, and may be shaped to contour the finger 156. The elastomer 150 provides an air seal between the finger 156 and the opening 120, which leads into the reservoir 102. Thus, in some embodiments, the durometer range of the finger pad/elastomer 150 may be between Shore 20A and 40A, specifically, the range may be between Shore 20A and 30A. In other embodiments, the durometer of the finger pad/elastomer may be 5A to 15A. Typical products known in the art include "Bumpon" or adhesive foam (manufactured by 3M), "Sorbothane" (manufactured by Trelleborg AB), and other gels commonly used in orthotics.

The lancet 110 may include a proximal end 112 and a distal end 114. The distal end 114 of the lancet 110 is coupled to a driver, such as a diaphragm 106. Hence, the diaphragm 106 drives the lancet 110. In one embodiment, the proximal end 112 of the lancet 110 is perpendicular to the bottom surface 116 of the sampling assembly 100, and is concentric with the opening 120. Moreover, the proximal end 112 of the lancet 110, which is used to puncture the skin, is configured such that the proximal end 112 is prevented from protruding out of the bottom surface 116 prior to the lancing operation. In one embodiment, the diameter of the lancet 110 is substantially the same as the diameter of the opening 120 to provide smooth sliding movement for the lancet 110 through the opening 120.

In the illustrated embodiment of FIG. 1, the shaft of the lancet 110 passes through the check valve 122 to hold the valve 122 open prior to the lancing operation. In one embodiment, the check valve 122 may be configured as a sample inflow valve such as a duckbill check valve. In this embodiment, the opening 120 may be connected to the reservoir 102 through the check valve 122. Thus, the reservoir 102 may be formed as a portion of the elliptical chamber 104 that is lined by the diaphragm 106. In the illustrated embodiment, the lower portion of the chamber 104 lined by the diaphragm 106 forms the reservoir 102. In some embodiments, the diaphragm 106 may be formed with an elastomer of harder durometer type compounds and/or less permeability than the finger pad 150. Thus, in this embodiment, the durometer range of the diaphragm/elastomer 106 may be between Shore 20A and 80A, specifically, the range may be between Shore 30A and 60A. In other embodiments, the diaphragm 106 may be formed with any suitable material for properly actuating the lancet 110.

Figure 2A:
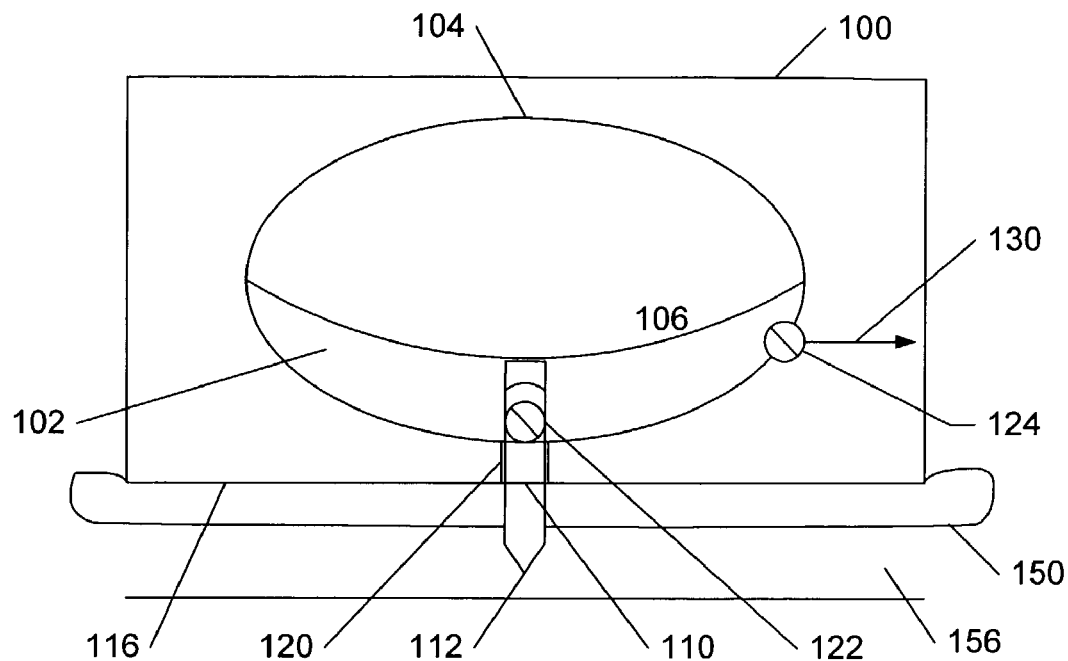
FIG. 2A illustrates a cut-away side view showing the movement of the diaphragm and the lancet when the lancet is protracted out of the bottom surface in accordance with an embodiment of the invention.
Figure 2B:
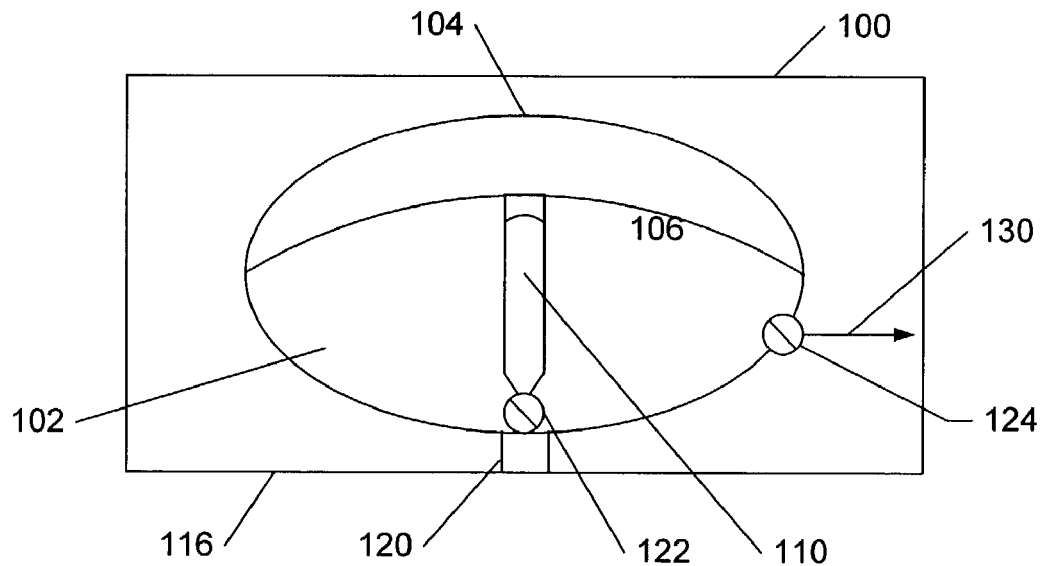
FIG. 2B illustrates a cut-away side view showing the movement of the diaphragm and the lancet when the lancet is retracted into the chamber beyond the check valve in accordance with an embodiment of the invention.

FIGS. 2A and 2B show the movement of the diaphragm 106 and the lancet 110 when the lancet 110 is protracted out of the bottom surface 116 (i.e. actuated) and is retracted into the chamber 104 beyond the check valve 122, respectively, in accordance with an embodiment of the invention. Hence, when the lancet 110 is protracted out of the bottom surface 116 (see FIG. 2A), the sampling assembly 100 is performing the lancing operation. As the lancet 110 is being retracted, negative pressure created within the reservoir 102 suctions and transfers the blood sample from the lanced skin area. When the lancet 110 is substantially retracted (see FIG. 2B), the check valve 122 closes and the blood sample is stored in an air tight enclosure 102. In one embodiment, the chamber 104 may be primed with nitrogen or other inert gas for the collection of blood samples.

The diaphragm 106 is shaped to deflect downwardly during actuation and is volumetrically dimensioned to contain at its fully retracted position a blood sample volume appropriate for test and/or analysis. In one embodiment, an appropriate blood sample volume is approximately 1–5 microliters.

The diaphragm 106 as shown in FIG. 1 is in a neutral position, i.e. prior to being actuated. When the diaphragm 106 is actuated, as shown in FIG. 2A, the diaphragm 106 compresses and flexes in the direction toward the finger 156. The diaphragm 106 may be actuated using piezoelectric, electromagnetic, vacuum/pressure (e.g. pneumatic), or any other suitable method. Thus, the actuation of the diaphragm 106 drives the proximal end 112 of the lancet 110 to puncture the finger 156 through the finger pad 150. Once the finger 156 has been punctured, the diaphragm 106 actuation is reversed, and the lancet 110 is retracted into the chamber 104 beyond check valve 122, as shown in FIG. 2B, so that the shaft of the lancet 110 no longer holds the valve 122 open. As the diaphragm 106 is actuated in the reverse direction, the diaphragm 106 depresses and flexes in the direction away from the finger 156. This creates negative pressure within the reservoir 102 and suctions the blood sample from the lanced area (not shown) of the finger 156 through the pad 150, through opening 120, and through check valve 122. The check valve 122 allows flow only in the distal direction away from the finger 156. Once the appropriate volume of blood has been suctioned from the lanced area into the reservoir 102, the check valve 122 is closed. The blood sample may then be siphoned through check valve 124 to the blood outflow conduit 130 for blood gas analysis. Therefore, the check valves 122, 124 regulate inflow and outflow, respectively, of the blood sample into and out of the reservoir 102. Furthermore, the blood sample suctioned from the lanced area is substantially prevented from being exposed and contaminated with ambient air.

In an alternative embodiment of actuation, the diaphragm 106 can be stretched proximally analogous to cocking a spring. The stretched diaphragm 106 is then released with the energy stored in the stretched diaphragm 106 converted to kinetic energy driving the lancet 110 into the finger. Once the lancet 110 has reached the maximum displacement (governed by the extent of the stretched diaphragm 106), the lancet 110 returns to the initial rest position with an equal and opposite energy. This restoring force of the diaphragm 106 retracts the lancet 110 from the finger.

Upon completion of the lancing operation, the lancet 110 is withdrawn from the check valve 122. Thus, the lancet 110 can no longer penetrate the check valve 122. Therefore, this embodiment of the sampling device 100 allows only a single use of the device for a safety precaution. The sampling device 100 may be manufactured as a simple molded device with relatively compact dimensions, making the material and construction inexpensive and therefore suitable for a disposable device. Furthermore, the flat design profile and ergonomic nature of the device lends itself to handheld point-of-care devices.

In some embodiments, a sensor (not shown) may be located on a surface, e.g. the surface 116, of the sampling assembly 100. The sensor may then be activated when the finger 156 is positioned on the proximal side 152 of the finger pad 150 such that there is substantially no air gap between the pad 150 and the finger 156. Thus, the sensor may be used to indicate that the configuration of the sampling assembly 100 and the finger pad 150 forms a closed system around the lanced area of the finger 156, and is ready to extract blood sample from the lanced area. An example of such a sensor is the piezoelectric design as described in a U.S. Patent Application (Inventors: Freeman, et al., entitled "TISSUE PENETRATION DEVICE", Ser. No. 10/127,395) and assigned to the same assignee.

Figure 3:
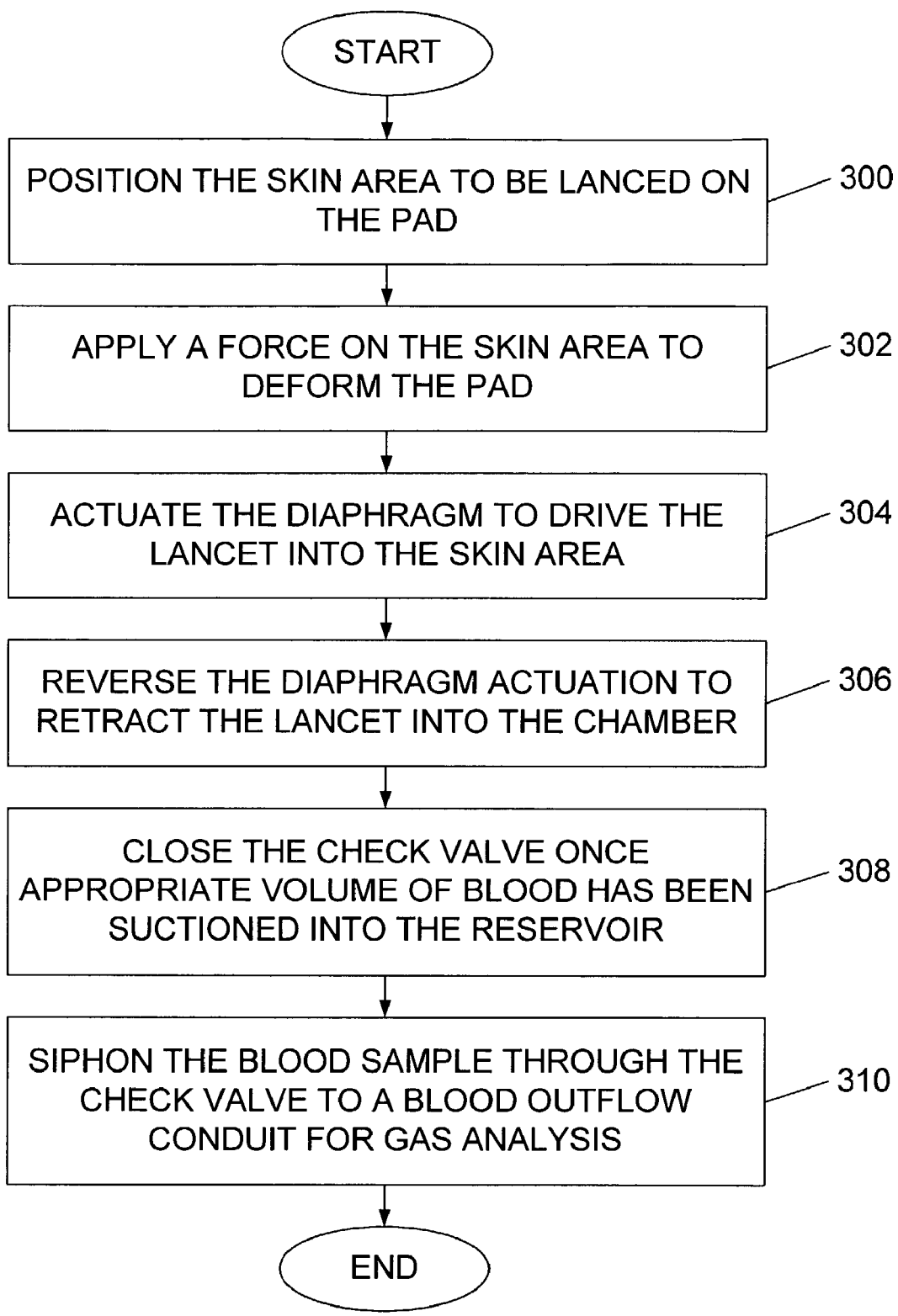
FIG. 3 is a flowchart describing a technique for lancing and obtaining a blood sample according to an embodiment of the invention.
Figure 4:
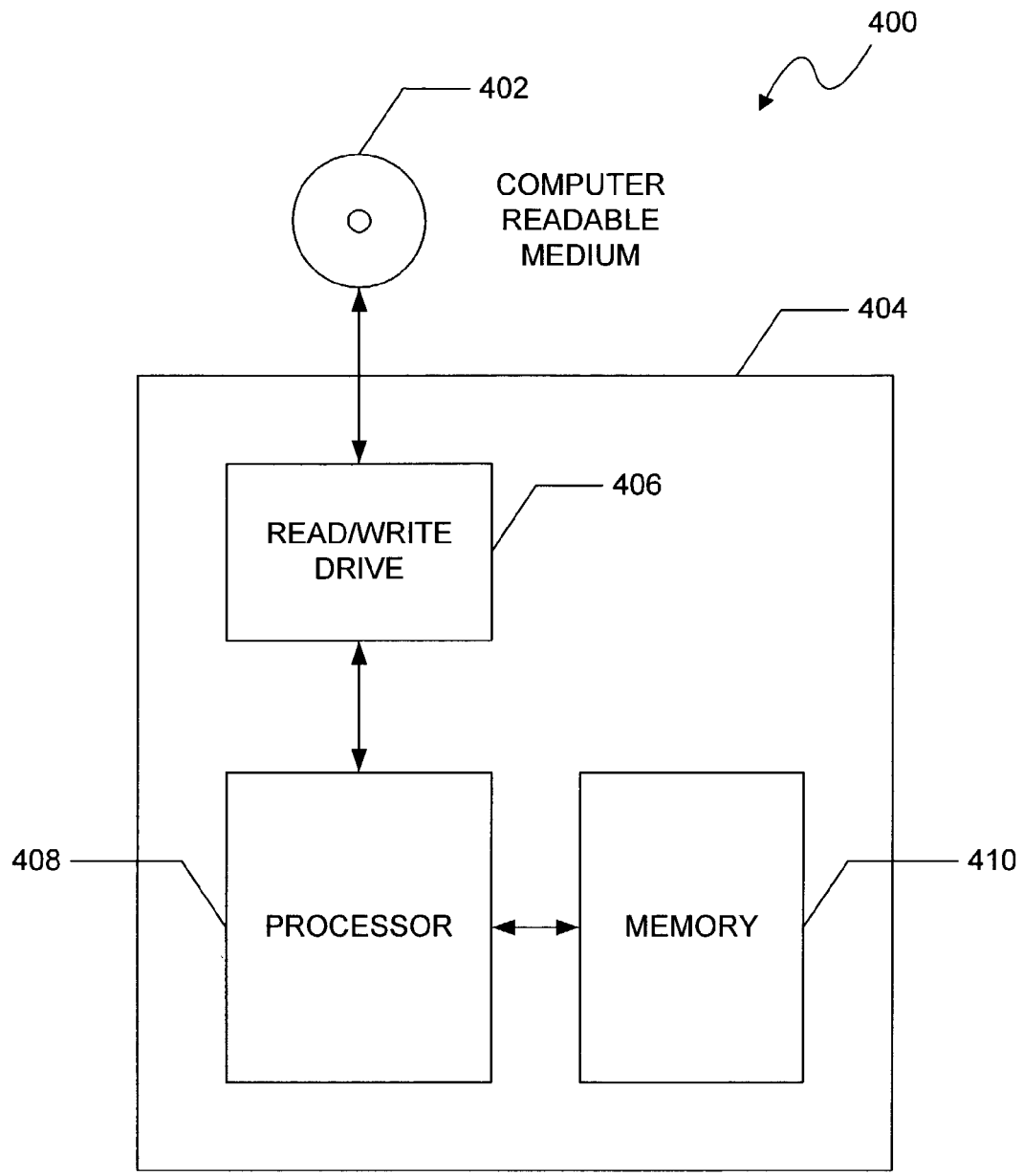
FIG. 4 is a block diagram of a processor-based system which may execute codes residing on the computer readable medium.

FIG. 3 is a flowchart describing a technique for lancing and obtaining a blood sample in a sealed configuration according to an embodiment of the invention. In the illustrated embodiment, the blood sample is obtained without substantial exposure to ambient air to enable substantially accurate blood gas analysis. In some embodiments, the technique may use the above-described blood sampling device (see FIG. 1) which includes the sampling assembly 100 and the finger pad 150. In other embodiments, the technique may use other devices suitable for obtaining the blood sample without substantial exposure to ambient air. These other devices may include an apparatus which measures the skin area (e.g. finger) and performs the lancing operation automatically by employing the below-described method (FIG. 3) in a processor-based system (FIG. 4).

In the illustrated embodiment of FIG. 3, a skin area to be lanced, such as finger 156, is positioned on the finger pad 150, at 300. A force is then applied on the finger 156 to deform the pad 150, at 302, so that the finger pad 150 forms a sealed configuration around the skin area to transfer blood from the skin area of the finger 156 into the reservoir 102 of the sampling assembly 100 without exposing the blood to ambient air. In one embodiment, this force may activate a sensor to actuate the lancing operation. In an alternative embodiment, the sensor may offer an electronic confirmation of correct finger placement such as a visual or audible signal. At 304, the diaphragm 106 is actuated to drive the lancet 110 into the skin area. The driving of the lancet 110 into the skin area punctures the skin area to draw the blood sample. The actuation may be initiated either by the user using a trigger after recognizing the signal or automatically by the sensor which has sensed the force applied by the finger 156.

Once the skin area has been punctured, actuation of the diaphragm 106 is reversed, at 306, and the lancet 110 is retracted into the chamber 104. Movement of the diaphragm 106 in the reverse direction creates negative pressure within the reservoir 102 and suctions the blood sample from the lanced skin area of the finger 156 in a sealed configuration. Once the appropriate volume of blood has been suctioned from the lanced area into the reservoir 102, the check valve 122 is closed, at 308. The blood sample may then be siphoned through the check valve 124 to the blood outflow conduit 130, at 310, for blood gas analysis.

The diaphragm 106 may be actuated using piezoelectric, electromagnetic, vacuum/pressure (e.g. pneumatic), or any other suitable method. The actuation of the diaphragm 106 drives the proximal end 112 of the lancet 110 to puncture the finger 156 through the finger pad 150. Piezoelectric actuation drives the lancet 110 using vibrations on the diaphragm 106. Electromagnetic actuation drives the lancet 110 using a magnetic field as described in a U.S. Patent Application (Inventors: Freeman et al., entitled "TISSUE PENETRATION DEVICE", Ser. No. 10/127,395) and assigned to the same assignee. The vacuum actuation drives the lancet 110 using back pressure to diaphragm 106 to advance the lancet 110 and suction behind diaphragm 106 to retract the lancet 110.

A block diagram of a processor-based system 400 which may execute codes residing on the computer readable medium 402 is shown in FIG. 4. The codes are related to methods and means for lancing and obtaining a blood sample in a sealed configuration described in conjunction with FIGS. 1 through 3. Initially, codes operate to sense that a sealed configuration around a skin area has been formed to transfer blood from the skin area into a blood reservoir without exposing the blood to ambient air. A driver, such as diaphragm 106, is then actuated to drive the lancet 110 into the skin area to lance the skin area within the sealed configuration. Once the skin area has been punctured, actuation of the diaphragm 106 is reversed, and the lancet 110 is retracted into the chamber 104. Movement of the diaphragm 106 in the reverse direction creates negative pressure within the reservoir 102 and suctions the blood sample from the lanced skin area of the finger 156 in a sealed configuration. Once the appropriate volume of blood has been suctioned from the lanced area into the reservoir 102, the check valve 122 is closed. The blood sample may then be siphoned through the check valve 124 to the blood outflow conduit 130 for blood gas analysis.

The computer readable medium 402 may be a fixed medium such as read-only memory (ROM). A read/write drive 406 in the computer 404 reads the code on the computer readable medium 402. The code is then executed in the processor 408. The processor 408 may access the computer main memory 410 to store or retrieve data.

There has been disclosed herein embodiments for lancing and obtaining a blood sample in a substantially sealed configuration to enable substantially accurate gas analysis of the sample. The lancing operation may utilize a sampling device comprising an elastomer disposed between a sampling assembly and a target skin area.

While specific embodiments of the invention have been illustrated and described, such descriptions have been for purposes of illustration only and not by way of limitation. For example, even though the illustrated embodiments show a finger pad, it is understood that this may include any pad that substantially prevents exposure of the blood sample to ambient air during lancing operation of a skin area. Accordingly, throughout this detailed description, for the purposes of explanation, numerous specific details were set forth in order to provide a thorough understanding of the present invention. It will be apparent, however, to one skilled in the art that the embodiments may be practiced without some of these specific details. For example, although the illustrated embodiment of FIG. 4 shows a system 400 having a computer 404 with fixed and removable disks 402, the system 400 may be configured as a handheld computer with medium 402 and memory 410 integrated into the processor 408. For another example, although the illustrated embodiment of FIG. 1 shows two check valves 122, 124, the lancing and blood sampling operation may be performed using only one valve for both suctioning of the blood sample from the lanced skin area and for siphoning the sample from the reservoir for analysis. In other instances, well-known structures and functions were not described in elaborate detail in order to avoid obscuring the subject matter of the present invention. Accordingly, the scope and spirit of the invention should be judged in terms of the claims which follow.

What is claimed is:

1. A blood sampling device, comprising:
    a sampling assembly including a driver, a lancet, and a blood reservoir, said lancet having a proximal end and a distal end; and
    a pad having a proximal side and a distal side, said proximal side conforming to the shape of a skin area, and said distal side attached to the sampling assembly, said pad and said sampling assembly configured to provide a sealed configuration around the skin area for transferring blood from the skin area to said reservoir;
    wherein the driver is electromagnetically actuated to move the lancet from a first position to a second position to pierce the skin area;
    wherein the driver includes a diaphragm coupled to the lancet, said diaphragm to drive said lancet.

2. The blood sampling device of claim 1, wherein said pad includes relatively soft durometer type material.

3. The blood sampling device of claim 2, wherein said material includes silicone rubber.

4. The blood sampling device of claim 1, wherein said diaphragm is formed with an elastomer of harder durometer type material than said pad.

5. The blood sampling device of claim 1, wherein said diaphragm is formed with an elastomer of less permeability than said pad.

6. The blood sampling device of claim 1, wherein said diaphragm compresses and flexes toward the skin area when said diaphragm is actuated and said lancet is protracted out.

7. The blood sampling device of claim 1, wherein said diaphragm creates suction upon retraction of said lancet.

8. The blood sampling device of claim 1, wherein said blood reservoir is enclosed by said diaphragm and said sampling assembly.

9. The blood sampling device of claim 8, further comprising:
    an opening on a surface of said sampling assembly, said opening configured to provide a conduit for the blood sample into the reservoir.

10. The blood sampling device of claim 9, wherein said surface of said sampling assembly is coupled to the distal side of said pad.

11. The blood sampling device of claim 9, wherein said proximal end of the lancet is approximately perpendicular to said surface of the sampling assembly, and is concentric with said opening.

12. The blood sampling device of claim 9, further comprising:
    a first valve coupled to said opening, said first valve to regulate inflow of the blood sample into said reservoir.

13. The blood sampling device of claim 12, wherein said lancet passes through said first valve to hold said first valve open prior to piercing the skin area.

14. The blood sampling device of claim 12, wherein said first valve includes a duckbill check valve.

15. The blood sampling device of claim 8, further comprising:
    a second valve to enable outflow of the blood sample from said reservoir.

16. The blood sampling device of claim 9, further comprising:
    a sensor disposed on the surface of said sampling assembly, said sensor configured to detect when said proximal side of said pad conforms to the shape of said skin area.

17. A device, comprising:
    a blood sampling assembly having a surface with an opening, said sampling assembly including:
        a lancet having a proximal end and a distal end, said proximal end configured with respect to said surface of said sampling assembly to pierce a finger tip;
        a driver coupled to the distal end of said lancet to drive the lancet from a first position to a second position to pierce skin, wherein the driver is electromagnetically actuated;
        a blood reservoir enclosed by said driver and said sampling assembly;
        a first valve fitted to said opening, said first valve kept open by said lancet prior to piercing said finger tip, said first valve to control transfer of blood from said finger tip into said blood reservoir; and
    a finger pad disposed between said finger tip and said sampling assembly, said finger pad configured to enable transfer of blood from said finger tip to said blood reservoir in a sealed configuration, wherein a proximal side of the finger pad conforms to the shape of a skin area, and a distal side attached to the sampling assembly;
    wherein retracting the lancet from the second position back into the blood sampling assembly creates negative pressure that draws blood into the blood reservoir;
    wherein said driver includes a diaphragm volumetrically dimensioned to contain at a fully retracted position a blood sample volume appropriate for blood analysis.

18. The device of claim 17, wherein said first valve is closed by withdrawal of said lancet from the first valve upon completion of lancing operation to allow only a singe use of said sampling assembly.

19. The device of claim 17, further comprising:
    a blood outflow conduit to enable outflow of the blood from said reservoir for analysis.

20. The device of claim 19, further comprising:
    a second valve coupled between said reservoir and said blood outflow conduit to regulate the outflow of the blood.

21. A method, comprising:
    positioning a skin area to be lanced on a pad;

applying a force on said skin area to allow the pad to conform to the shape of said skin area, and to configure said skin area in a scaled configuration;

lancing said skin area through said pad using a lancet driven by a driver that is electromagnetically actuated; and drawing a blood sample from said lanced skin area through said pad to collect the blood sample without substantially exposing the blood sample to ambient air;

wherein said lancing includes actuating and compressing a diaphragm to drive the lancet into said skin area.

22. The method of claim 21, further comprising:
providing a reservoir to store the collected blood sample.

23. The method of claim 22, wherein said suctioning includes allowing a lancet to keep a first valve open to provide an inflow conduit for the blood sample flowing into said reservoir.

24. The method of claim 23, wherein said suctioning includes retracting the lancet beyond said first valve such that said first valve is closed once appropriate volume of the blood sample has been collected in said reservoir.

25. The method of claim 24, wherein said suctioning includes depressing a diaphragm to create a negative pressure.

26. The method of claim 21, further comprising:
dispensing said collected blood sample through a second valve for blood analysis.

27. A computer readable medium containing executable instructions which when executed in a processing system, performs lancing operation and obtains a blood sample from a finger tip in a sealed configuration, said executable instructions comprising:

sensing to confirm that a sealed configuration around a skin area has been formed to transfer blood from the skin area into a blood reservoir without exposing the blood to ambient air;

lancing said skin area within the sealed configuration using a lancet driven by a driver that is electromagnetically actuated; and transferring the blood sample from said lanced skin area in the sealed configuration;

wherein said lancing includes actuating a diaphragm to drive a lancet.

28. The medium of claim 27, wherein said sensing includes detecting to confirm that a pad coupled to said skin area conforms to the shape of said skin area.

29. The medium of claim 27, wherein said sensing includes detecting to confirm that a pad forms a seal around an opening in said blood reservoir.

30. A method, comprising:
positioning a skin area to be lanced on a pad;

applying a force on said skin area to allow the pad to conform to the shape of said skin area, and to configure said skin area in a sealed configuration;

lancing said skin area through said pad using a lancet driven by a driver that is electromagnetically actuated; and drawing a blood sample from said lanced skin area through said pad to collect the blood sample without substantially exposing the blood sample to ambient air;

providing a reservoir to store the collected blood sample;

wherein said suctioning includes allowing a lancet to keep a first valve open to provide an inflow conduit for the blood sample flowing into said reservoir;

wherein said suctioning includes retracting the lancet beyond said first valve such that said first valve is closed once appropriate volume of the blood sample has been collected in said reservoir;

wherein said suctioning includes depressing a diaphragm to create a negative pressure.

* * * * *